US009309347B2

(12) United States Patent
Concagh et al.

(10) Patent No.: US 9,309,347 B2
(45) Date of Patent: Apr. 12, 2016

(54) BIORESORBABLE THERMOSET POLYESTER/URETHANE ELASTOMERS

(75) Inventors: Danny Concagh, Medfield, MA (US); Chang Cheng You, Burlington, MA (US); Greg Zugates, Chelmsford, MA (US)

(73) Assignee: Biomedical, Inc., Watertown, MA (US)

( * ) Notice: Subject to any disclaimer, the term of this patent is extended or adjusted under 35 U.S.C. 154(b) by 75 days.

(21) Appl. No.: 13/253,720

(22) Filed: Oct. 5, 2011

(65) Prior Publication Data
US 2012/0142884 A1 Jun. 7, 2012

Related U.S. Application Data

(63) Continuation-in-part of application No. 12/783,261, filed on May 19, 2010, now Pat. No. 8,137,396.

(60) Provisional application No. 61/179,834, filed on May 20, 2009, provisional application No. 61/227,308, filed on Jul. 21, 2009, provisional application No. 61/251,984, filed on Oct. 15, 2009.

(51) Int. Cl.
| | |
|---|---|
| C08G 18/42 | (2006.01) |
| C08G 18/72 | (2006.01) |
| A61L 31/06 | (2006.01) |
| C08G 18/73 | (2006.01) |
| C08G 63/08 | (2006.01) |
| C08G 63/91 | (2006.01) |
| A61F 2/90 | (2013.01) |
| A61L 31/10 | (2006.01) |
| A61L 31/16 | (2006.01) |
| C08G 18/77 | (2006.01) |

(52) U.S. Cl.
CPC ............. *C08G 18/4266* (2013.01); *A61F 2/90* (2013.01); *A61L 31/06* (2013.01); *A61L 31/10* (2013.01); *A61L 31/16* (2013.01); *C08G 18/428* (2013.01); *C08G 18/4269* (2013.01); *C08G 18/4277* (2013.01); *C08G 18/72* (2013.01); *C08G 18/73* (2013.01); *C08G 18/771* (2013.01); *C08G 63/08* (2013.01); *C08G 63/912* (2013.01)

(58) Field of Classification Search
CPC ...... C08G 63/08; C08G 63/912; C08G 18/72; C08G 18/73; C08G 18/4266; C08G 18/4269; C08G 18/4277; C08G 18/428
USPC .................. 525/415, 440.01, 440.04, 440.13, 525/440.15, 410, 411, 450, 454
See application file for complete search history.

(56) References Cited

U.S. PATENT DOCUMENTS

| | | | |
|---|---|---|---|
| 2,957,831 A * | 10/1960 | Parker ............................ | 521/115 |
| 3,150,114 A * | 9/1964 | Rockoff ........................... | 528/81 |
| 4,243,775 A | 1/1981 | Rosensaft et al. | |
| 4,300,565 A | 11/1981 | Rosensaft et al. | |
| 4,461,298 A | 7/1984 | Shalaby et al. | |
| 4,643,734 A | 2/1987 | Lin | |
| 4,804,691 A * | 2/1989 | English et al. ................. | 523/118 |
| 4,916,193 A | 4/1990 | Tang et al. | |
| 4,920,203 A | 4/1990 | Tang et al. | |
| 4,990,158 A | 2/1991 | Kaplan et al. | |
| 5,066,772 A | 11/1991 | Tang et al. | |
| 5,145,945 A | 9/1992 | Tang et al. | |
| 5,185,408 A | 2/1993 | Tang et al. | |
| 5,213,580 A | 5/1993 | Slepian et al. | |
| 5,256,764 A | 10/1993 | Tang et al. | |
| 5,274,074 A | 12/1993 | Tang et al. | |
| 5,356,423 A | 10/1994 | Tihon | |
| 5,412,068 A | 5/1995 | Tang et al. | |
| 5,449,372 A | 9/1995 | Schmaltz et al. | |
| 5,468,253 A * | 11/1995 | Bezwada et al. .............. | 606/230 |
| 5,486,593 A | 1/1996 | Tang et al. | |
| 5,516,781 A | 5/1996 | Morris | |
| 5,531,735 A | 7/1996 | Thompson | |
| 5,562,725 A | 10/1996 | Schmitt | |
| 5,563,146 A | 10/1996 | Morris | |
| 5,578,662 A * | 11/1996 | Bennett et al. .................. | 524/54 |
| 5,595,751 A | 1/1997 | Bezwada et al. | |
| 5,616,608 A | 4/1997 | Kinsella | |
| 5,634,946 A | 6/1997 | Slepian | |
| 5,650,447 A | 7/1997 | Keefer | |

(Continued)

FOREIGN PATENT DOCUMENTS

| | | |
|---|---|---|
| EP | 1308473 | 5/2003 |
| EP | 724436 | 1/2004 |

(Continued)

OTHER PUBLICATIONS

Bhowmick, A.K.; Current Topics in Elastomer Research, 2008, p. 228-230.*

(Continued)

*Primary Examiner* — Robert Jones, Jr.
(74) *Attorney, Agent, or Firm* — Kacvinsky Daisak Bluni PLLC

(57) ABSTRACT

Bioresorbable thermoset elastomers and methods of making the same are disclosed. In certain embodiments, the thermoset elastomers include soft segments comprising branched polyesters, and hard segments including urethane and/or urea. The thermoset elastomers are made in certain embodiments by curing a branched prepolymer with a cross-linking agent. In certain embodiments, the mechanical properties of the thermoset elastomers are tailored by selecting the average molecular weight of the prepolymer, or by tuning the ratio of prepolymer to the cross-linking agent during curing, or by selecting a cross-linking agent with specific chemical characteristics.

28 Claims, 5 Drawing Sheets

(56) References Cited

U.S. PATENT DOCUMENTS

| | | |
|---|---|---|
| 5,665,077 A | 9/1997 | Rosen |
| 5,665,728 A | 9/1997 | Morris |
| 5,676,963 A | 10/1997 | Keefer |
| 5,703,200 A | 12/1997 | Bezwada |
| 5,716,981 A | 2/1998 | Hunter |
| 5,733,925 A | 3/1998 | Kunz |
| 5,741,325 A | 4/1998 | Chaikof |
| 5,762,625 A | 6/1998 | Igaki |
| 5,766,710 A | 6/1998 | Turnlund |
| 5,788,979 A | 8/1998 | Alt et al. |
| 5,797,877 A | 8/1998 | Hamilton et al. |
| 5,799,384 A | 9/1998 | Schwartz et al. |
| 5,824,053 A | 10/1998 | Khosravi |
| 5,834,582 A | 11/1998 | Sinclair |
| 5,851,217 A | 12/1998 | Wolff |
| 5,871,535 A | 2/1999 | Wolff |
| 5,899,935 A | 5/1999 | Ding |
| 5,968,091 A | 10/1999 | Pinchuk et al. |
| 5,984,957 A | 11/1999 | Laptewicz |
| 5,993,972 A | 11/1999 | Reich et al. |
| 5,994,444 A | 11/1999 | Trescony |
| 5,997,468 A | 12/1999 | Wolff et al. |
| 6,004,346 A | 12/1999 | Wolff et al. |
| 6,004,573 A | 12/1999 | Rathi et al. |
| 6,005,020 A | 12/1999 | Loomis |
| 6,051,021 A | 4/2000 | Frid |
| 6,074,659 A | 6/2000 | Kunz |
| 6,074,660 A | 6/2000 | Jamiolkowski et al. |
| 6,083,257 A | 7/2000 | Taylor |
| 6,083,524 A | 7/2000 | Sawhney et al. |
| 6,087,479 A | 7/2000 | Stamler |
| 6,117,949 A | 9/2000 | Rathi et al. |
| 6,120,536 A | 9/2000 | Ding |
| 6,153,252 A | 11/2000 | Hossainy et al. |
| 6,161,399 A | 12/2000 | Jayaraman |
| 6,171,232 B1 | 1/2001 | Papandreou |
| 6,171,609 B1 | 1/2001 | Kunz |
| 6,179,051 B1 | 1/2001 | Ayub |
| 6,193,746 B1 | 2/2001 | Strecker |
| 6,221,100 B1 | 4/2001 | Strecker |
| 6,221,997 B1 | 4/2001 | Woodhouse et al. |
| 6,232,434 B1 | 5/2001 | Stamler |
| 6,238,687 B1 | 5/2001 | Mao et al. |
| 6,240,978 B1 | 6/2001 | Gianotti |
| 6,245,103 B1 | 6/2001 | Stinson |
| 6,249,952 B1 | 6/2001 | Ding |
| 6,261,594 B1 | 7/2001 | Smith |
| 6,268,390 B1 | 7/2001 | Kunz |
| 6,270,779 B1 | 8/2001 | Fitzhugh |
| 6,284,305 B1 | 9/2001 | Ding |
| 6,290,722 B1 | 9/2001 | Wang |
| 6,295,714 B1 | 10/2001 | Roychowdhury |
| 6,299,604 B1 | 10/2001 | Ragheb |
| 6,299,636 B1 | 10/2001 | Schmitt |
| 6,306,421 B1 | 10/2001 | Kunz |
| 6,315,791 B1 | 11/2001 | Gingras et al. |
| 6,338,739 B1 | 1/2002 | Datta |
| 6,342,068 B1 | 1/2002 | Thompson |
| 6,368,346 B1 | 4/2002 | Jadhav |
| 6,379,691 B1 | 4/2002 | Tedeschi |
| 6,403,635 B1 | 6/2002 | Kinsella |
| 6,403,759 B2 | 6/2002 | Stamler |
| 6,419,694 B1 | 7/2002 | Sandock |
| 6,423,092 B2 | 7/2002 | Datta |
| 6,429,232 B1 | 8/2002 | Kinsella |
| 6,451,337 B1 | 9/2002 | Smith |
| 6,471,978 B1 | 10/2002 | Stamler |
| 6,488,701 B1 | 12/2002 | Nolting et al. |
| 6,488,705 B2 | 12/2002 | Schmitt |
| 6,488,951 B2 | 12/2002 | Toone |
| 6,500,203 B1 | 12/2002 | Thompson et al. |
| 6,506,411 B2 | 1/2003 | Hunter |
| 6,514,515 B1 | 2/2003 | Williams |
| 6,515,009 B1 | 2/2003 | Kunz |
| 6,537,312 B2 | 3/2003 | Datta et al. |
| 6,544,544 B2 | 4/2003 | Hunter |
| 6,569,191 B1 | 5/2003 | Hogan |
| 6,569,195 B2 | 5/2003 | Yang |
| 6,585,764 B2 | 7/2003 | Wright |
| 6,589,546 B2 | 7/2003 | Kamath |
| 6,592,617 B2 | 7/2003 | Thompson |
| 6,599,928 B2 | 7/2003 | Kunz |
| 6,605,115 B1 | 8/2003 | Cooke |
| 6,632,242 B2 | 10/2003 | Igaki |
| 6,632,446 B1 | 10/2003 | Hubbell et al. |
| 6,645,518 B2 | 11/2003 | Tedeschi |
| 6,656,506 B1 | 12/2003 | Wu et al. |
| 6,656,966 B2 | 12/2003 | Garvey |
| 6,663,881 B2 | 12/2003 | Kunz |
| 6,706,274 B2 | 3/2004 | Herrmann |
| 6,719,934 B2 | 4/2004 | Stinson |
| 6,730,064 B2 | 5/2004 | Ragheb |
| 6,737,447 B1 | 5/2004 | Smith |
| 6,743,462 B1 | 6/2004 | Pacetti |
| 6,753,454 B1 | 6/2004 | Smith |
| 6,776,796 B2 | 8/2004 | Falotico |
| 6,790,228 B2 | 9/2004 | Hossainy |
| 6,805,898 B1 | 10/2004 | Wu et al. |
| 6,808,536 B2 | 10/2004 | Wright |
| 6,855,366 B2 | 2/2005 | Smith |
| 6,869,973 B2 | 3/2005 | Garvey |
| 6,875,840 B2 | 4/2005 | Stamler |
| 6,884,429 B2 | 4/2005 | Koziak |
| 6,887,266 B2 | 5/2005 | Williams et al. |
| 6,887,485 B2 | 5/2005 | Fitzhugh |
| 6,908,622 B2 | 6/2005 | Barry |
| 6,932,930 B2 | 8/2005 | DeSimone et al. |
| 6,949,112 B1 | 9/2005 | Sridharan et al. |
| 6,974,475 B1 | 12/2005 | Wall |
| 6,991,647 B2 | 1/2006 | Jadhav |
| 6,997,948 B2 | 2/2006 | Stinson |
| 7,005,137 B1 | 2/2006 | Hossainy et al. |
| 7,008,397 B2 | 3/2006 | Tweden |
| 7,011,678 B2 | 3/2006 | Tenerz |
| 7,029,495 B2 | 4/2006 | Stinson |
| 7,063,884 B2 | 6/2006 | Hossainy et al. |
| 7,070,615 B1 | 7/2006 | Igaki |
| 7,087,709 B2 | 8/2006 | Stamler |
| 7,101,566 B2 | 9/2006 | Rosenblatt et al. |
| 7,141,061 B2 | 11/2006 | Williams et al. |
| 7,160,323 B2 | 1/2007 | Pulnev et al. |
| 7,160,592 B2 | 1/2007 | Rypacek et al. |
| 7,163,554 B2 | 1/2007 | Williams et al. |
| 7,163,562 B2 | 1/2007 | Datta et al. |
| 7,166,133 B2 | 1/2007 | Evans et al. |
| 7,217,286 B2 | 5/2007 | Falotico |
| 7,220,816 B2 | 5/2007 | Pacetti et al. |
| 7,223,286 B2 | 5/2007 | Wright |
| 7,229,473 B2 | 6/2007 | Falotico |
| 7,252,679 B2 | 8/2007 | Fischell et al. |
| 7,279,005 B2 | 10/2007 | Stinson |
| 7,279,175 B2 | 10/2007 | Chen |
| 7,285,287 B2 | 10/2007 | Williams et al. |
| 7,291,165 B2 | 11/2007 | Rosenthal |
| 7,292,885 B2 | 11/2007 | Scott |
| 7,300,662 B2 | 11/2007 | Falotico |
| 7,318,945 B2 | 1/2008 | Thornton |
| 7,348,319 B2 | 3/2008 | Hrabie |
| 7,348,364 B2 | 3/2008 | Shalaby |
| 7,361,726 B2 | 4/2008 | Pacetti et al. |
| 7,378,106 B2 | 5/2008 | Hossainy |
| 7,387,641 B2 | 6/2008 | Schmitt |
| 7,390,333 B2 | 6/2008 | Dutta |
| 7,416,559 B2 | 8/2008 | Shalaby |
| 7,419,502 B2 | 9/2008 | Pulnev et al. |
| 7,419,503 B2 | 9/2008 | Pulnev et al. |
| 7,419,504 B2 | 9/2008 | Hossainy |
| 7,425,218 B2 | 9/2008 | Keefler |
| 7,438,712 B2 | 10/2008 | Chouinard |
| 7,445,628 B2 | 11/2008 | Ragheb |
| 7,470,283 B2 | 12/2008 | Dutta et al. |
| 7,488,444 B2 | 2/2009 | Furst et al. |
| 7,491,233 B1 | 2/2009 | Ding |
| 7,491,234 B2 | 2/2009 | Palasis et al. |

(56) References Cited

U.S. PATENT DOCUMENTS

| | | | |
|---|---|---|---|
| 7,498,385 B2 | 3/2009 | Swetlin et al. |
| 7,504,125 B1 | 3/2009 | Pacetti et al. |
| 7,517,338 B2 | 4/2009 | Freyman et al. |
| RE40,816 E | 6/2009 | Taylor et al. |
| 7,556,842 B2 | 7/2009 | Worsham et al. |
| 7,563,483 B2 | 7/2009 | Hossainy et al. |
| 7,585,516 B2 | 9/2009 | Pacetti |
| 7,594,928 B2 | 9/2009 | Headley, Jr. et al. |
| 7,604,699 B2 | 10/2009 | Chen et al. |
| 7,611,533 B2 | 11/2009 | Bates et al. |
| 7,618,448 B2 | 11/2009 | Schmitz |
| 7,648,725 B2 | 1/2010 | Van Sciver et al. |
| 7,658,880 B2 | 2/2010 | Wu |
| 7,682,647 B2 | 3/2010 | Hossainy et al. |
| 7,682,648 B1 | 3/2010 | Ding et al. |
| 7,718,213 B1 | 5/2010 | Scheer |
| 7,731,740 B2 | 6/2010 | Lafont et al. |
| 7,736,386 B2 | 6/2010 | Pulnev et al. |
| 7,758,908 B2 | 7/2010 | Pham et al. |
| 7,761,968 B2 | 7/2010 | Huang et al. |
| 7,763,068 B2 | 7/2010 | Pulney et al. |
| 7,763,308 B2 | 7/2010 | Chen et al. |
| 7,776,381 B1 | 8/2010 | Tang et al. |
| 7,776,382 B2 | 8/2010 | Chappa et al. |
| 7,794,495 B2 | 9/2010 | Gale et al. |
| 7,794,776 B1 | 9/2010 | Limon et al. |
| 7,794,777 B2 | 9/2010 | Kokish et al. |
| 7,833,261 B2 | 11/2010 | Chen et al. |
| 7,857,844 B2 | 12/2010 | Norton et al. |
| 7,875,233 B2 | 1/2011 | Huang et al. |
| 7,875,283 B2 | 1/2011 | Hossainy et al. |
| 7,879,953 B2 | 2/2011 | Pacetti |
| 7,901,452 B2 | 3/2011 | Gale et al. |
| 7,919,162 B2 | 4/2011 | DeSimone et al. |
| 7,923,022 B2 | 4/2011 | Wang et al. |
| 7,951,185 B1 | 5/2011 | Abbate et al. |
| 7,971,333 B2 | 7/2011 | Gale et al. |
| 7,972,616 B2 | 7/2011 | Debrow et al. |
| 7,985,441 B1 | 7/2011 | Tang et al. |
| 8,003,156 B2 | 8/2011 | Van Sciver |
| 8,016,879 B2 | 9/2011 | Gale et al. |
| 8,043,553 B1 | 10/2011 | Durcan |
| 8,058,470 B2 * | 11/2011 | Uyama et al. | 560/182 |
| 8,137,396 B2 | 3/2012 | Busold et al. |
| 2004/0044405 A1 | 3/2004 | Wolff |
| 2004/0106987 A1 | 6/2004 | Palasis |
| 2004/0181277 A1 | 9/2004 | Furst |
| 2004/0260272 A1 | 12/2004 | Friedman et al. |
| 2005/0142315 A1 | 6/2005 | DeSimone et al. |
| 2005/0214343 A1 | 9/2005 | Tremble |
| 2005/0214344 A1 | 9/2005 | Barrows et al. |
| 2006/0002977 A1 | 1/2006 | Dugan |
| 2006/0100568 A1 | 5/2006 | Tan |
| 2006/0121087 A1 | 6/2006 | Williams et al. |
| 2006/0147492 A1 | 7/2006 | Hunter et al. |
| 2006/0195059 A1 | 8/2006 | Freyman et al. |
| 2006/0204738 A1 | 9/2006 | Dubrow et al. |
| 2006/0246108 A1 | 11/2006 | Pacetti et al. |
| 2007/0026132 A1 | 2/2007 | Williams et al. |
| 2007/0038284 A1 | 2/2007 | Williams et al. |
| 2007/0093889 A1 | 4/2007 | Wu et al. |
| 2007/0110787 A1 | 5/2007 | Hossainy et al. |
| 2007/0123539 A1 | 5/2007 | Wu |
| 2007/0255422 A1 | 11/2007 | Wei et al. |
| 2007/0271763 A1 | 11/2007 | Huang et al. |
| 2007/0280851 A1 | 12/2007 | Freeman et al. |
| 2007/0281250 A1 | 12/2007 | Aono |
| 2007/0282247 A1 | 12/2007 | Desai et al. |
| 2007/0283552 A1 | 12/2007 | Gale et al. |
| 2007/0299504 A1 | 12/2007 | Gale et al. |
| 2008/0008739 A1 | 1/2008 | Hossainy et al. |
| 2008/0091262 A1 | 4/2008 | Gale et al. |
| 2008/0145393 A1 | 6/2008 | Trollsas et al. |
| 2008/0147161 A1 | 6/2008 | Chen et al. |
| 2008/0147164 A1 | 6/2008 | Gale et al. |
| 2008/0177375 A1 | 7/2008 | Chen et al. |
| 2008/0255267 A1 * | 10/2008 | Domb et al. | 523/124 |
| 2008/0275539 A1 | 11/2008 | Williams et al. |
| 2008/0300669 A1 | 12/2008 | Hossainy |
| 2008/0306592 A1 | 12/2008 | Wang |
| 2009/0005860 A1 | 1/2009 | Gale et al. |
| 2009/0018643 A1 | 1/2009 | Hashi et al. |
| 2009/0062904 A1 | 3/2009 | Furst |
| 2009/0099600 A1 | 4/2009 | Moore et al. |
| 2009/0138076 A1 | 5/2009 | Palasis et al. |
| 2009/0216104 A1 | 8/2009 | DeSimone et al. |
| 2009/0285974 A1 | 11/2009 | Kerrigan et al. |
| 2009/0286761 A1 | 11/2009 | Cheng et al. |
| 2009/0304769 A1 | 12/2009 | Kunkel et al. |
| 2010/0198344 A1 | 8/2010 | Omura et al. |
| 2010/0298952 A1 | 11/2010 | Busold et al. |
| 2011/0238162 A1 | 9/2011 | Busold et al. |
| 2011/0319987 A1 | 12/2011 | Palasis et al. |

FOREIGN PATENT DOCUMENTS

| | | | |
|---|---|---|---|
| EP | 1382628 | | 1/2004 |
| EP | 1400218 | | 4/2004 |
| EP | 1700872 | | 9/2006 |
| GB | 2475778 | | 6/2011 |
| JP | 2003-246851 | * | 5/2003 ............ C08G 63/06 |
| WO | 9934750 | | 7/1999 |
| WO | WO 2008029527 A1 * | 3/2008 |
| WO | 2008/076383 | | 6/2008 |
| WO | 2009/158290 | | 12/2009 |

OTHER PUBLICATIONS

IUPAC Compendium of Chemical Terminology, Definition of Elastomer, 2014.*

Hietala et al., Thrombosis and Haemostatis, "Platelet deposition on stainless steel, spiral, and braided polylactide stents", 92(6):1394-1401, (2004).

International Search Report dated Jul. 21, 2010 for International Patent Application No. PCT/US2010/035417, (2pgs).

G.A. Abraham, A. Marcos-Fernandez, J.S. Roman, Bioresorbable poly(ester-ether urethanes) from L-lysine diisocyanate and triblock copolymers with different hydrophilic character, J. Biomed. Mater. Res. A 2006 76, 729-736.

P. Bruin, J. Smedinga, A. J. Pennings, M.F. Jonkman, Biodegradable lysine diisocyanate-based poly(glycolide-co-ϵ-caprolactone)-urethane network in artificial skin, Biomaterials 1990, 11, 291-295.

A. O. Helminen, H. Korhonen, J. V. Seppala, Cross-linked poly(ϵ-caprolactone/D,L-lactide) copolymers with elastic properties, Macromol. Chem. Phys. 2002, 203, 2630-2639.

L. Pinchuck, et al. (2008) Medical applications of poly(styrene-block-isobutyelene-blockstyrene) ("SIBS"), Biomaterials, 29, 448-460.

J.E. Puskas, et al. (2004) Biomedical application of commercial polymers and novel polyisobutylene-based thermoplastic elastomers for soft tissue replacement, Biomacromolecules, 5, 1141-1154.

J.E. Puskas, et al. (2009) Drug-eluting stent coatings, Wiley Interdiscip, Rev. Nanomed, Nanobiotechnol., 1, 451-462.

Examination Report dated Jan. 21, 2011, issued in GB Application No. GB1008366.5.

Search and Examination Report dated Sep. 1, 2010 issued in GB Application No. GB1008366.5.

Examination Report dated May 5, 2011, issued in GB Application No. GB1008366.5.

Examination Report dated Jul. 27, 2012 in European Patent Application No. GB1019777.0.

Examination Report dated Feb. 6, 2013 in United Kingdom Patent Application No. GB1222543.9.

* cited by examiner

A.

B.

BIORESORBABLE THERMOSET POLYESTER/URETHANE ELASTOMERS

This application is a continuation-in-part of, and claims the benefit of priority to, U.S. patent application Ser. No. 12/783,261, filed May 19, 2010, now U.S. Pat. No. 8,137,396 by inventors Lee Core et al., entitled "Medical Implant," and further claims the benefit of priority to U.S. Patent Application 61/179,834, filed May 20, 2009, by inventors Lee Core et al., entitled "Medical Implant," to U.S. Patent Application 61/227,308, filed Jul. 21, 2009, by inventors Lee Core et al., entitled "Medical Implant," and to U.S. Patent Application 61/251,984, filed Oct. 15, 2009, by inventors Lee Core et al.

TECHNICAL FIELD

The present invention relates to bioresorbable thermoset polyester/urethane elastomers and methods of making and using the same.

BACKGROUND

Bioresorbable elastomers are synthetic polymers that are broken down in vivo and can be used, for example, as coatings for stents and catheters, as drug delivery systems, as vascular grafts, as scaffolds for tissue engineering, and as guides for nerve growth. Examples of medical devices coated with such polymers are disclosed in U.S. patent application Ser. No. 12/783,261, the entire content of which is disclosed herein by reference. To achieve their widest utility, elastomers should be able to mimic the resilience, flexibility, and tensile strength exhibited by natural materials and encountered in a wide range of potential medical applications. However, bioresorbable elastomers currently known in the art have not simultaneously achieved high tensile strength, flexibility and low permanent deformation under cyclic mechanical use that approach what is found in nature. Accordingly, there is a need for a bioresorbable elastomer that combines high tensile strength with a high degree of flexibility and low permanent deformation.

SUMMARY OF THE INVENTION

The present invention addresses the need described above by providing bioresorbable elastomers and methods of making the same. The bioresorbable elastomers of the present invention have a range of applications, including but not limited to vascular grafts, drug delivery systems, stent coatings to improve radial recovery, and as tissue engineering substrates including nerve guides, small blood vessels, bladders, cardiac tissues, cartilages, tendons, and ligaments.

In one aspect, the present invention relates to bioresorbable elastomers that include a branched prepolymer and an isocyanate crosslinker and that have high tensile strength and a high degree of flexibility along with low permanent deformation under cyclic mechanical use.

In another aspect, the present invention relates to a method of making such a bioresorbable elastomer by providing a branched prepolymer and crosslinking it with an isocyanate crosslinker.

In still another aspect, the present invention relates to a method of optimizing the mechanical characteristics of a bioresorbable elastomer by optimizing the crosslink density and/or the average molecular weight of branched subunits. In certain embodiments, the tensile strength, flexibility, and long-term deformation of a bioresorbable elastomer are optimized by providing a symmetrical isocyanate crosslinker having a plurality of isocyanate moieties of equal reactivity during the curing of the bioresorbable elastomer. In other embodiments, these characteristics are optimized by adjusting the average molecular weight of the prepolymer used during production of the bioresorbable elastomer. In yet other embodiments, these characteristics are optimized by adjusting the ratio of prepolymer to cross-linker during production of the bioresorbable elastomer.

DETAILED DESCRIPTION

Figure 1:
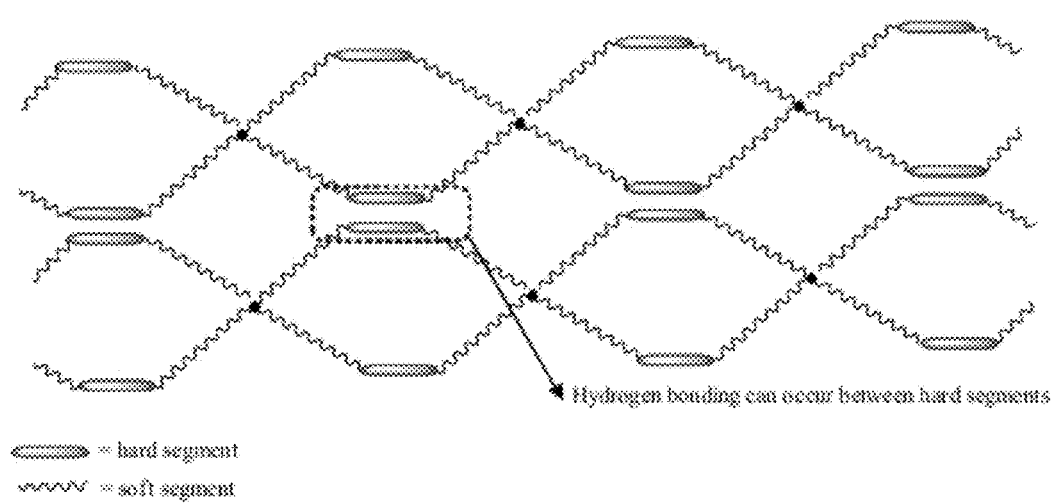
FIG. 1 is a schematic illustration of a thermoset elastomer of the present invention.

Bioresorbable thermoset elastomers (hereinafter, "elastomers") of the present invention simultaneously exhibit high elongation at break, low permanent deformation, and high tear resistance; by contrast, other bioresorbable elastomers currently known in the art do not simultaneously exhibit all of these characteristics. Elastomers of the present invention achieve this balance of properties by tuning the balance between chemical crosslinking via covalent bonding with physical crosslinking via non-covalent interactions. Elastomers of the invention comprise "soft" segments including branched polyesters, and "hard" segments including urethane or urea, as depicted in FIG. 1. These elastomers are formed by cross-linking branched prepolymers with cross-linking elements. In preferred embodiments, the prepolymers are branched polyesters, and the cross-linking elements are multifunctional isocyanates. Additionally, while the exemplary embodiments disclosed herein focus on "four arm" polyester prepolymers it will be understood by those skilled in the art that any branched prepolymer (n=3 or greater) with an appropriate glass transition temperature can be used to make elastomers of the present invention. It is expected that elastomers sharing some or all of the beneficial characteristics described above could be made comprising linear polymers crosslinked with branched multi-functional cross-linking elements.

Elastomers of the present invention exhibit good strength, high elasticity and a high degree of elastic recovery under cyclic mechanical strain. These properties are due to the optimized crosslinked nature—the degree of crosslinking—of these branched prepolymers crosslinked with isocyanates in combination with the phase separation of the "soft" (polyester) and "hard" (urethane/urea) segments. The soft segments of the elastomer permit elongation of the material while the hard segments impart strength. The combination of the hard and soft segments impart elasticity. The tensile strength and elongation to break of these elastomers can be adjusted by varying the crosslink density. If the crosslink density is high the resultant elastomer is strong with low permanent deformation but has a low elongation to break. Alternatively if the crosslink density is too low the elastomer has a high elongation to break but is weak, tacky and has high permanent deformation. Additional strength may also be obtained from secondary bonds that form between adjacent polymer chains; these are primarily hydrogen bonds between the hard (urethane/urea) segments of these elastomers. Phase separation of the hard and soft segments will also add to the high elasticity and low permanent deformation associated with these elastomers.

Elasticity and tensile strength of the elastomers can be optimized by adjusting the molecular weight and structure of the prepolymer, the structure of the isocyanate crosslinker, and the ratio of prepolymer to crosslinker used in the curing process. In a preferred embodiment, the average molecular weight (Mn) of the 4-arm prepolymer is at least 20,000 g/mol (i.e., 20 kDa), and more preferably at least 30,000 g/mol (i.e., 30 kDa). At the beginning of the curing process, the isocyanate cross-linker can be provided in a ratio of between 5 to 1 and 120 to 1 (mol/mol) relative to the prepolymer.

In certain preferred embodiments, the prepolymer is a 4 arm polymer such as poly (glycolide-co-ε-caprolactone) (50:50) (PGCL) or poly (lactide-co-ε-caprolactone) (50:50) (PLCL). Other multi-arm polymers, such as the block or random copolymers of glycolide and/or lactide with poly(ε-caprolactone), poly(butylene succinate) (PBS), poly(p-dioxanone) (PDO), and Poly(trimethylene carbonate) (PTMC), may also be used as the prepolymers. The ratio of the individual monomers is not limited to 50:50 and any other ratios are valid unless the glass transition temperature of the resultant copolymers is above room temperature.

The crosslinker used in the present invention is any suitable symmetrical isocyanate. In certain preferred embodiments, hexamethylene diisocyanate (HDI) is used as the cross-linker, and the polyester prepolymer is provided in a ratio of between 3 to 1 and 20 to 1 (wt/wt) relative to HDI.

Table 1 relates the mechanical properties of elastomers of the present invention made with PGCL and HDI including young's modulus, ultimate tensile strength and elongation to break measured on INSTRON according to standard procedures (Dey, J. et al. (2008), Biomaterials 29: 4638-4649). Mechanical tests were carried out at room temperature in air or at 37° C. in water. The table shows the impact of varying the average molecular weight of the PGCL prepolymer from 20,000 g/mol to 100,000 g/mol, and varying the quantity of HDI provided relative to the PGCL. It is noted that the mechanical properties are determined by both the molecular weight of the prepolymer and also by the ratio of prepolymer: HDI used. Increasing molecular weight of the prepolymer results in more elastic materials. For a given molecular weight increasing the wt:wt ratio of HDI:polymer results in a stronger elastomer.

TABLE 1

Mechanical properties of PGCL-HDI films with different PGCL prepolymer molecular weights

| Sample ID | Materials | E/MPa | $S_{max}$/MPa | $\gamma_b$/% |
|---|---|---|---|---|
| 101-034-01 | PGCL (20k)/HDI (12:1 wt/wt) | 5.7 | 5.4 | 350 |
| 101-034-02 | PGCL (20k)/HDI (12:2 wt/wt) | 4.5 | 3.0 | 310 |
| 101-034-03 | PGCL (20k)/HDI (12:3 wt/wt) | 37 | 5.4 | 280 |
| 101-034-04 | PGCL (20k)/HDI (12:4 wt/wt) | 43 | 7.5 | 320 |
| 089-090-01 | PGCL (100k)/HDI (20:1 wt/wt) | 4.2 | 7.3 | 820 |
| 089-090-02 | PGCL (100k)/HDI (20:2 wt/wt) | 3.9 | 9.0 | 860 |
| 089-090-03 | PGCL (100k)/HDI (20:3 wt/wt) | 6.0 | 6.7 | 700 |
| 089-090-04 | PGCL (100k)/HDI (20:4 wt/wt) | 10 | 9.6 | 810 |

Where E = Young's Modulus, S = Tensile strength and $\gamma_b$ = elongation at break
All measurements were made at room temperature in air.

Table 2 relates mechanical properties of elastomers of the present invention made with PLCL and HDI. The PLCL/HDI elastomers behave similarly to the PGCL/HDI elastomers in that as molecular weight is increased from 8 k to 100 k the elongation to break increases. Additionally, for the lower molecular weight prepolymers, regardless of the ratio of prepolymer to isocyanate, the materials are stiff and have low elongation to break. Generally, PGCL based elastomers are stronger than PLCL based elastomers of similar molecular weight, and PGCL based elastomers have different degradation rates than PLCL based elastomers.

TABLE 2

Mechanical properties of PLCL-HDI films with different PLCL molecular weights

| Sample ID | Materials | E/MPa | $S_{max}$/MPa | $\gamma_b$/% |
|---|---|---|---|---|
| 089-087-02 | PLCL (8k)/HDI (5:1 wt/wt) | 7.1 | 3.7 | 220 |
| 089-087-03 | PLCL (8k)/HDI (5:2 wt/wt) | 36.3 | 6.2 | 190 |
| 101-018-01 | PLCL (20k)/HDI (4:1 wt/wt) | 18.7 | 6.0 | 420 |
| 101-005-03 | PLCL (40k)/HDI (8:1 wt/wt) | 3.9 | 3.9 | 700 |
| 089-085-01 | PLCL (100k)/HDI (20:1 wt/wt) | 2.0 | 2.6 | 940 |
| 089-085-02 | PLCL (100k)/HDI (10:1 wt/wt) | 4.6 | 3.7 | 670 |

Where E = Young's Modulus, S = Tensile strength and $\gamma_b$ = elongation at break
All measurements were made at room temperature in air.

Table 3 sets forth the mechanical properties of polyester/urethane thermoset elastomers disclosed in the literature and measured on INSTRON according to standard procedures as discussed above. The thermoset elastomers listed in this table were prepared from a polyester prepolymer—poly(1,8-octanediol-co-citrate) (POC)—and then crosslinked with HDI. Although the elastomers of Table 3 are quite stiff, their elongation to break is far inferior to the elastomers of the present invention.

TABLE 3

Mechanical properties of POC-HDI films

| Materials | E (MPa) | S (MPa) | $\gamma_b$ (%) |
|---|---|---|---|
| POC:HDI (1:0.6 mol:mol) | 2.99 | 16.0 | 252 |
| POC:HDI (1:0.9 mol:mol) | 5.84 | 32.1 | 278 |
| POC:HDI (1:1.2 mol:mol) | 29.8 | 33.4 | 261 |

Where CUPE = crosslinked urethane doped polyesters

In addition to the molecular weight of the polyester prepolymer and ratio of prepolymer:isocyanate used, the choice of isocyanate cross-linker is also important in determining the final mechanical properties of the final elastomer. In a preferred embodiment, a symmetrical cross-linker is used, which has a plurality of isocyanate moieties of equal reactivity.

In certain embodiments, a catalyst may be used to catalyze the formation of the elastomer or a reaction involved therein, such as a gelling reaction. Any suitable catalyst may be used, including Zinc Octoate, Tin Octoate, Aluminum tris(acetylacetonate), etc. The type of catalyst used, or the absence of a catalyst, may influence the time and temperature required to fully cure the elastomer as shown in Table 4:

TABLE 4

Elastomer curing conditions using various catalysts or no catalyst

| Catalyst | Curing condition |
|---|---|
| No catalyst | 100° C., 16 hrs |
| 0.1% Zinc Octoate (Zn(Oct)$_2$) | 60° C., 16 hrs |

TABLE 4-continued

Elastomer curing conditions using various catalysts or no catalyst

| Catalyst | Curing condition |
|---|---|
| 0.2% Tin Octoate (Sn(Oct)$_2$) | 70° C., 16 hrs |
| 0.5% Aluminum tris(acetylacetonate) (Al(acac)$_3$) | 70° C., 40 hrs |

Figure 5:
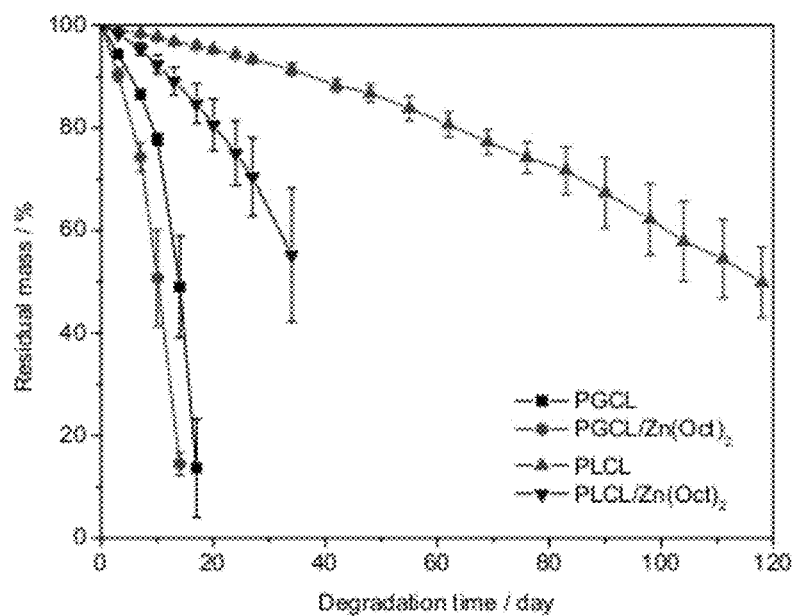
FIG. 5 is a representative plot of the degradation rates of polymers made with or without the polyurethane catalyst Zinc Octoate.

Surprisingly, the rate of degradation of elastomers of the invention (as measured by elastomer mass loss rate) is also affected by the presence or absence of a catalyst as shown in FIG. 5. Mass loss profiles of various PGCL and PLCL elastomers were established under degradation conditions in pH 12 buffer at 37° C., the elastomers were cured in the absence and presence of the catalyst Zn(Oct)$_2$.

The following examples illustrate aspects of the current invention in preferred embodiments without limitation of the spirit or scope of the claimed invention.

Example 1

Synthesis of 4-Arm PGCL Prepolymer

Figure 2:
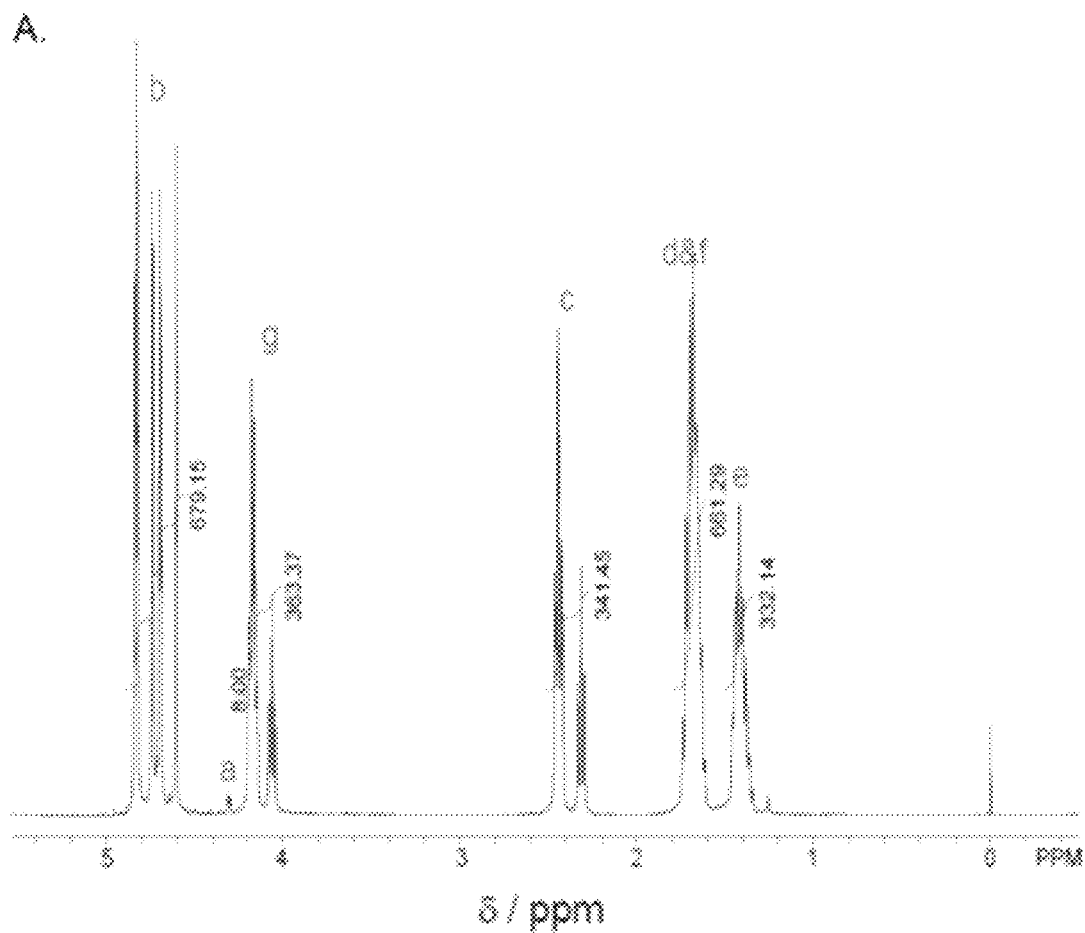
FIG. 2 is a representative $^1$H NMR spectrum of a 4-arm prepolymer of the present invention.
Figure 2:
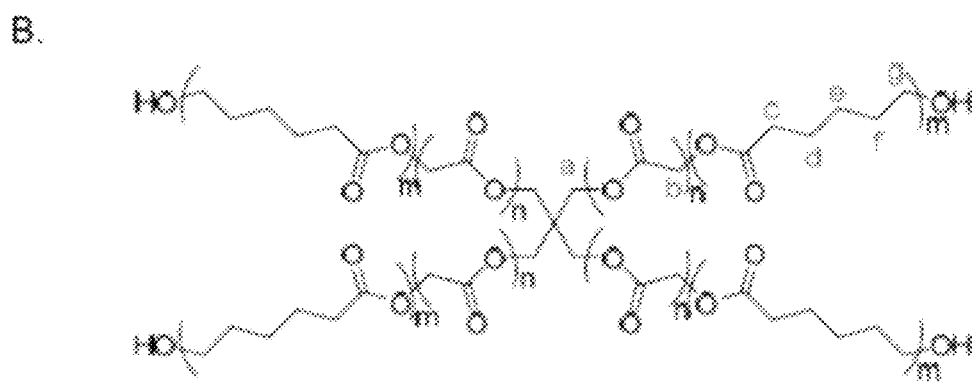

A 250 mL round-bottom flask was dried in oven at 110° C. and then cooled down to room temperature under a nitrogen atmosphere. Then, the flask was charged successively with Sn(Oct)$_2$ (90 mg), pentaerythritol (400 mg), glycolide (60.0 g), and ε-caprolactone (60.0 g). Subsequently, the flask was equipped with a magnetic stirrer bar and a three-way valve connected to a nitrogen balloon. The flask was thoroughly degassed under reduced pressure and flushed with nitrogen. This process took 2-3 h. The flask was then placed into an oil bath (with 1000 mL silica oil) which was preheated to 185° C. The temperature of the oil bath quickly dropped to 155~160° C. Meanwhile, the solid in the flask started to melt. Under vigorous stirring, the liquid in the flask became clear after 1~2 min. Generally, the stirrer bar stopped within 5 min due to an increase in the viscosity of the liquid. The reaction was continued at 170° C. for another 22 h under a nitrogen atmosphere. After cooling to room temperature, the solid obtained was dissolved in ca. 300~400 mL dichloromethane. The solution was filtered through a sintered glass funnel (pore size 70~100 μm) to remove the insoluble particulate (e.g. polyglycolide) and then precipitated from 1000~1200 mL anhydrous diethyl ether in a 1500 mL glass beaker. The solution was decanted and the residual sticky solid was washed with diethyl ether (150 mL×3). Subsequently, the beaker containing the materials was transferred to a vacuum oven operating at 55~60° C. After 3 d, the fully dried polymer material was taken out and transferred to a polypropylene bottle for storage. Typically, around 110 g polymer could be recovered. A $^1$H NMR spectrum of the purified polymer in CDCl$_3$ is shown in FIG. 2. GPC characterization with polystyrenes as standards gives an average molecular weight (Mn) of 40,000 g/mol and a polydispersity index (PDI) of 1.23. The molecular weight of the prepolymer can be varied by adjusting the molar ratio of monomer:initiator.

Example 2

Fabrication of Thermoset PEU Elastomeric Films

A 4-arm PGCL (50:50) Mn 40000 g/mol (1.0 g) and hexamethylene diisocyanate (HDI) 125 μL were dissolved in 10 mL dichloromethane. The solution was placed in a aluminum pan with diameter of 9 cm. The solvent was evaporated at room temperature (ca. 20° C.) for 3 h. The residual film was cured in a 100° C. oven for 16 h.

Example 3

Varying Mechanical Properties Depending Choice of Cross-Linker and Ratio of Cross-Linker to Prepolymer Films were prepared in a similar manner to that outlined in Example 2 using a prepolymer PLCL (50:50) Mn of 56000 g/mol and either an asymmetric isocyanate, lysine diisocyanate (LDI), or a symmetrical one, (HDI, as crosslinking agent. The films were cured in the presence of 0.1% zinc octoate at 60° C. for 20 hrs. Table 4 shows resulting mechanical properties of films prepared from PLCL 50:50 prepolymer using several varying ratios of LDI and HDI. The ratio of isocyanate to prepolymer (NCO:OH) was optimized to maximize the mechanical properties.

TABLE 4

Mechanical properties of PLCL-LDI & PLCL-HDI films with different mol:mol ratio NCO:OH

Figure 3:
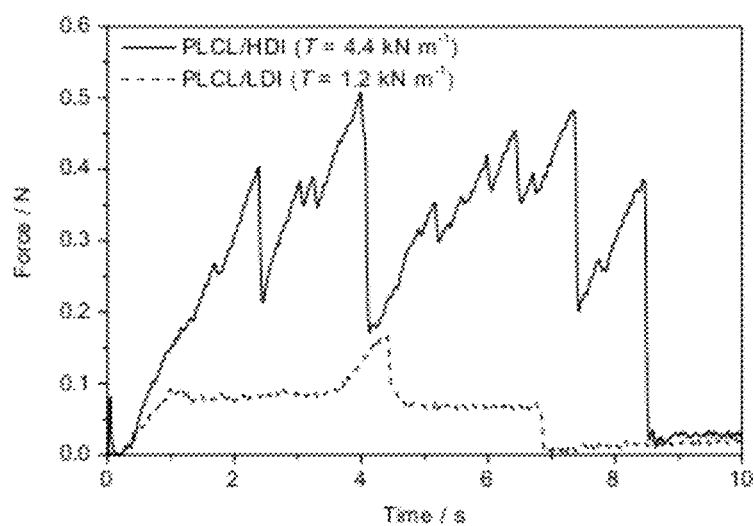
FIG. 3 is a representative plot of the relative tear strengths of two different thermoset elastomers of the present invention.

| Sample ID | Iso-cyanate | NCO:OH (mol:mol) | E (MPa) | $S_{max}$ (MPa) | γb (%) | T (kN m$^{-1}$) |
|---|---|---|---|---|---|---|
| 113-021-04 | LDI | 1:1 | Film too tacky to measure mechanical properties | | | |
| 113-026-01 | LDI | 3:1 | 2.4 | 1.7 | 350 | 1.1 |
| 113-026-02 | LDI | 4:1 | 2.3 | 1.3 | 200 | 1.3 |
| 113-026-03 | LDI | 5:1 | 2.4 | 1.6 | 390 | 1.2 |
| 113-026-04 | LDI | 6:1 | Film too tacky to measure mechanical properties | | | |
| 101-155-01 | HDI | 15:1 | 7.2 | 4.5 | 360 | 4.4 |
| 101-155-02 | HDI | 30:1 | 10.7 | 5.5 | 320 | 11.0 |

Where E = Young's Modulus,
S = Tensile strength,
γ$_b$ = elongation to break, and
T = tear strength
All measurements were made at 37° C. in water FIG. 3 depicts tear strengths of films prepared from a PLCL (50:50) prepolymer Mn 56000 g/mol and crosslinked with either HDI or LDI. The HDI cured films have higher tear strengths compared to the LDI cured films.

Example 4

Effect of Elastomer Tear Strength on Performance of Coated Stents

Figure 4:
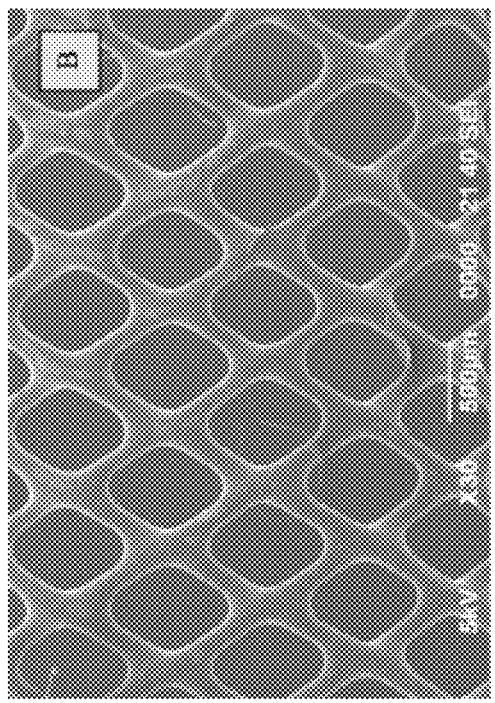
FIG. 4 is a comparative SEM micrograph showing stent coatings comprising thermoset elastomers of the present invention.
Figure 4:
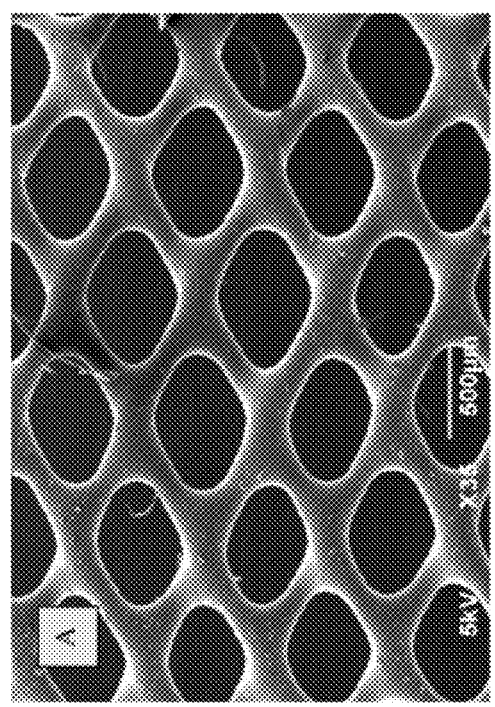

To illustrate how differences in tear strength affects elastomer performance in coatings, solutions of polyester PLCL prepolymer and an optimized ratio of crosslinker (HDI or LDI) were prepared in dichloromethane, spray coated onto a braided PLGA 75:25 stent structure and cured to form a conformal elastomeric coating. The PLGA stent structure has dimensions of 7 mm outer diameter and a length of 20 mm pre coating. Coated stents were then crimped to a diameter of 1.85 mm using a MSI radial force tester and then allowed to recover their original diameter. SEM images of the stent structure are then taken. FIG. 4 shows a braided device coated with LDI-cured elastomer (A) which displays cracks on its surface (arrows) post crimping. Note that the coating integrity remains intact in the case of a braided device coated with an HDI-cured elastomer (B).

The superior mechanical properties obtained from the HDI cured elastomer are due at least in part to the symmetrical nature of the crosslinker which symmetry allows it to crosslink in a homogenous manner when compared to LDI.

While various aspects and embodiments of the present invention have been described above, it should be understood that they have been presented by way of illustration rather than limitation. The breadth and scope of the present invention is intended to cover all modifications and variations that come within the scope of the following claims and their equivalents.

What is claimed is:

1. A polymer prepared by the process comprising the steps of:
    providing a branched polyester having at least three branches and having a glass transition temperature less than about 25° Centigrade, wherein the polyester has an average molecular weight (Mn) of at least 20,000 g/mol; and
    at least partially crosslinking said polyester with a symmetrical isocyanate cross linker,
    wherein said polymer is an elastomer.

2. The polymer of claim 1, wherein the polyester is Poly(lactide-co-ϵ-caprolactone).

3. The polymer of claim 2, wherein the isocyanate crosslinker is hexamethylene diisocyanate.

4. The polymer of claim 1, wherein the polyester is Poly(glycolide-co-ϵ-caprolactone).

5. The polymer of claim 4, wherein the isocyanate crosslinker is hexamethylene diisocyanate.

6. The polymer of claim 1, wherein the polyester is provided in a ratio of between 8:1 and 20:1 wt/wt relative to the isocyanate crosslinker during the crosslinking step.

7. The polymer of claim 1, wherein the isocyanate crosslinker is present in a ratio of between approximately 1:1 and 120:1 mol/mol relative to the polyester during the crosslinking step.

8. The polymer of claim 1, wherein the polyester has four branches.

9. The polymer of claim 1, wherein the isocyanate crosslinker comprises two or more isocyanate groups of equal reactivity.

10. The polymer of claim 1, wherein the isocyanate crosslinker is chosen for its lack of steric hindrance.

11. A polymer prepared by the process comprising the steps of:
    providing a branched prepolymer with an average molecular weight of between 33 kDa and 65 kDa, the prepolymer having at least three branches and having a glass transition temperature less than about 25° Centigrade; and
    curing said polymer with an isocyanate crosslinker.

12. The polymer of claim 11, wherein the prepolymer is a polyester.

13. The polymer of claim 11, wherein the isocyanate crosslinker is symmetrical.

14. The polymer of claim 11, wherein the prepolymer is Poly(lactide-co-ϵ-caprolactone.

15. The polymer of claim 14, wherein the isocyanate crosslinker is hexamethylene diisocyanate.

16. The polymer of claim 11, wherein the prepolymer is Poly(glycolide-co-ϵ-caprolactone.

17. The polymer of claim 16, wherein the isocyanate crosslinker is hexamethylene diisocyanate.

18. The polymer of claim 11, wherein the prepolymer is provided in a ratio of between 8:1 and 20:1 wt/wt relative to the isocyanate crosslinker during the curing step.

19. The polymer of claim 11, wherein the curing step takes place at 100° C.

20. The polymer of claim 11, wherein the curing step is performed over 16 hours.

21. The polymer of claim 11, wherein the method further comprises the steps of:
    dissolving the prepolymer and the isocyanate crosslinker in a solvent; and
    removing the solvent by evaporation.

22. The polymer of claim 1, wherein said polymer is a thermoset elastomer.

23. The polymer of claim 22, wherein said polymer is a bioresorbable thermoset elastomer.

24. The polymer of claim 1, wherein the polymer exhibits an elongation at break that ranges from 280% to 940%.

25. The polymer of claim 24, wherein the polyester has an average molecular weight (Mn) of at least 30,000 g/mol.

26. The polymer of claim 1, wherein the polyester has an average molecular weight (Mn) of at least 30,000 g/mol.

27. The polymer of claim 1, wherein the polyester has an average molecular weight (Mn) ranging from 30,000 g/mol to 100,000 g/mol.

28. The polymer of claim 26, wherein the polyester is Poly(lactide-co-ϵ-caprolactone) or Poly(glycolide-co-ϵ-caprolactone).

* * * * *